United States Patent [19]
Kitazawa et al.

[11] Patent Number: 6,046,192
[45] Date of Patent: Apr. 4, 2000

[54] PHENYLETHANOLAMINOTETRALIN-CARBOXAMIDE DERIVATIVES

[75] Inventors: Makio Kitazawa; Kosuke Okazaki; Tetsuro Tamai; Masaru Saito; Nobuyuki Tanaka; Hiroaki Kobayashi; Ken Kikuchi; Hideyuki Muranaka, all of Nagano, Japan

[73] Assignee: Kissei Pharmaceutical Co., Ltd., Tokyo, Japan

[21] Appl. No.: 09/155,478

[22] PCT Filed: Apr. 4, 1997

[86] PCT No.: PCT/JP97/01159

§ 371 Date: Mar. 8, 1999

§ 102(e) Date: Mar. 8, 1999

[87] PCT Pub. No.: WO97/38970

PCT Pub. Date: Oct. 23, 1997

[30] Foreign Application Priority Data

Apr. 12, 1996 [JP] Japan .................................. 8-126225

[51] Int. Cl.[7] ...................... A61K 31/165; A61K 31/445; A61K 31/535; C07C 233/16; C07D 295/185
[52] U.S. Cl. ...................... 514/237.5; 514/319; 514/424; 514/620; 544/168; 546/206; 548/540; 564/134
[58] Field of Search .................................. 514/237.5, 319, 514/424; 544/620, 168; 546/206; 548/540; 564/134

[56] References Cited
FOREIGN PATENT DOCUMENTS

99/09001  2/1999  WIPO .

Primary Examiner—Gary Geist
Assistant Examiner—Tadfiq A. Solola
Attorney, Agent, or Firm—Sughrue, Mion, Zinn Macpeak & Seas, PLLC

[57] ABSTRACT

The present invention relates to a phenylethanolaminotetralincarboxamide derivative represented by the general formula:

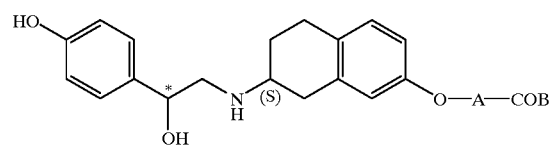

(wherein A represents a lower alkylene group; B represents an amino group, a di(lower alkyl)amino group or a 3 to 7-membered alicyclic amino group which may contain an oxygen atom in the ring; the carbon atom marked with * represents a carbon atom in (R) configuration, (S) configuration or a mixture thereof; and the carbon atom marked with (S) represents a carbon atom in (S) configuration) and a pharmaceutically acceptable salt thereof, which have a selective $\beta_2$-adrenergic receptor stimulating effect with relieved burdens on the heart such as tachycardia and are useful as an agent for the prevention of threatened abortion and premature labor, a bronchodilator, and an agent for pain remission and promoting stone removal in urolithiasis.

7 Claims, No Drawings

PHENYLETHANOLAMINOTETRALIN-CARBOXAMIDE DERIVATIVES

This Application is a 371 of PCT/JP97/01159 filed Apr. 4, 1997.

TECHNICAL FIELD

The present invention relates to novel phenylethanolaminotetralincarboxamide derivatives which are useful as medicaments.

More particularly, the present invention relates to phenylethanolaminotetralincarboxamide derivatives represented by the general formula:

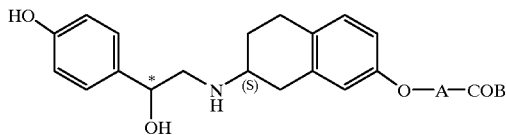

(I)

(wherein A represents a lower alkylene group; B represents an amino group, a di(lower alkyl)amino group or a 3 to 7-membered alicyclic amino group which may contain an oxygen atom in the ring; the carbon atom marked with * represents a carbon atom in (R) configuration, (S) configuration or a mixture thereof; and the carbon atom marked with (S) represents a carbon atom in (S) configuration) and pharmaceutically acceptable salts thereof, which have a selective $\beta_2$-adrenergic receptor stimulating effect with relieved burdens on the heart such as tachycardia.

BACKGROUND ART

As substituted phenylethanolaminotetralin derivatives, for example, compounds represented by the general formula:

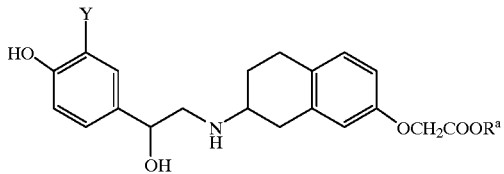

(wherein $R^a$ represents a hydrogen atom or an ethyl group; and Y represents a hydrogen atom or a chlorine atom), the hydrochloride or oxalate thereof, or single optical isomers thereof and a compound represented by the formula:

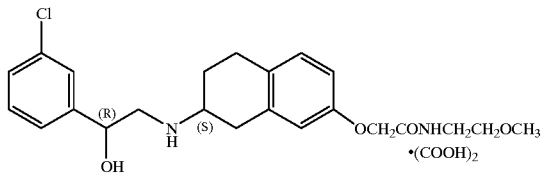

(wherein the carbon atom marked with (R) represents a carbon atom in (R) configuration; and the carbon atom marked with (S) represents a carbon atom in (S) configuration), which have gut selective sympathomimetic and antipollakiuria activities, have been disclosed (cf., published Japanese patent application (kohyo) No. Hei 6-506676 and published Japanese patent application (kohyo) No. Hei 6-506955). However, these compounds are $\beta_3$-adrenergic receptor stimulating agents having a remarkable $\beta_3$-adrenergic receptor stimulating effect.

DISCLOSURE OF INVENTION

The present invention relates to phenylethanolaminotetralincarboxamide derivatives represented by the general formula:

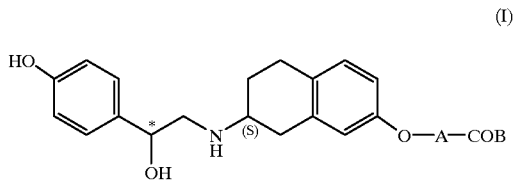

(I)

(wherein A represents a lower alkylene group; B represents an amino group, a di(lower alkyl)amino group or a 3 to 7-membered alicyclic amino group which may contain an oxygen atom in the ring; the carbon atom marked with * represents a carbon atom in (R) configuration, (S) configuration or a mixture thereof; and the carbon atom marked with (S) represents a carbon atom in (S) configuration) and pharmaceutically acceptable salts thereof.

The present invention relates to a pharmaceutical composition comprising the above phenylethanolaminotetralincarboxamide derivative or a pharmaceutically acceptable salt thereof.

The present invention relates to an agent for the prevention of threatened abortion and premature labor, a bronchodilator and an agent for pain remission and promoting stone removal in urolithiasis which comprises as the active ingredient the above phenylethanolaminotetralincarboxamide derivative or a pharmaceutically acceptable salt thereof.

The present invention relates to a method for the prevention of threatened abortion and premature labor, the prevention and treatment of diseases associated with bronchiostenosis and airway obstruction, and pain remission and promoting stone removal in urolithiasis which comprises administering the above phenylethanolaminotetralincarboxamide derivative or a pharmaceutically acceptable salt thereof.

The present invention relates to a use of the above phenylethanolaminotetralincarboxamide derivative or a pharmaceutically acceptable salt thereof for the manufacture of a pharmaceutical composition for the prevention of threatened abortion and premature labor, the prevention and treatment of diseases associated with bronchiostenosis and airway obstruction, and pain remission and promoting stone removal in urolithiasis.

Furthermore, the present invention relates to a use of the above phenylethanolaminotetralincarboxamide derivative or a pharmaceutically acceptable salt thereof as an agent for the prevention of threatened abortion and premature labor, a bronchodilator and an agent for pain remission and promoting stone removal in urolithiasis.

BEST MODE FOR CARRYING OUT THE INVENTION

In order to find an excellent $\beta_2$-adrenergic receptor stimulating agent, the inventors of the present invention made extensive studies and found that certain phenylethanolaminotetralincarboxamide derivatives represented by the above general formula (I) have a potent and selective $\beta_2$-adrenergic receptor stimulating effect and are remarkably useful as $\beta_2$-adrenergic receptor stimulating agents, thereby forming the basis of the present invention.

Accordingly, the present invention relates to phenylethanolaminotetralincarboxamide derivatives represented by the general formula:

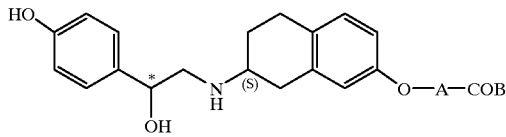
(I)

(wherein A represents a lower alkylene group; B represents an amino group, a di(lower alkyl)amino group or a 3 to 7-membered alicyclic amino group which may contain an oxygen atom in the ring; the carbon atom marked with * represents a carbon atom in (R) configuration, (S) configuration or a mixture thereof; and the carbon atom marked with (S) represents a carbon atom in (S) configuration) and pharmaceutically acceptable salts thereof, which have a $\beta_2$-adrenergic receptor stimulating effect with higher selectivity in comparison with a $\beta_1$-adrenergic receptor stimulating effect and with relieved burdens on the heart such as tachycardia.

In the compounds represented by the above general formula (I) of the present invention, the term "di(lower alkyl)amino group" means an amino group di-substituted by straight- or branched-chain alkyl group(s) having 1 to 6 carbon atoms (e.g., methyl, ethyl, propyl, isopropyl), such as a dimethylamino group, a diethylamino group, an ethylmethylamino group or the like. Also, the term "lower alkylene group" means a straight-chain alkylene group having 1 to 3 carbon atoms such as a methylene group, an ethylene group or a trimethylene group, and the term "3 to 7-membered alicyclic amino group which may contain an oxygen atom in the ring" means a 1-pyrrolidinyl group, a piperidino group, a morpholino group or the like.

The compounds represented by the above general formula (I) of the present invention can be prepared by the following procedure.

For example, the compounds of the present invention can be prepared by subjecting an amine compound represented by the general formula:

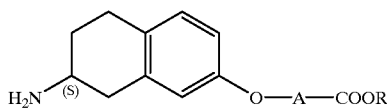
(II)

(wherein R represents a lower alkyl group; and A and the carbon atom marked with (S) have the same meanings as defined above) to N-alkylation using an alkylating agent represented by the general formula:

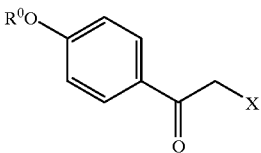
(III)

(wherein $R^0$ represents a hydroxy-protective group; and X represents a halogen atom), reducing the resulting compound in the usual way, removing the hydroxy-protective group as the occasion demands to give a compound represented by the general formula:

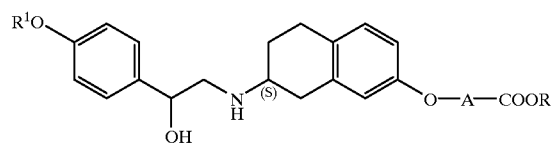
(IV)

(wherein $R^1$ represents a hydrogen atom or a hydroxy-protective group; and A, R and the carbon atom marked with (S) have the same meanings as defined above), subjecting the resulting compound to amidation in the usual way using an amine compound represented by the general formula:

B—H                                    (V)

(wherein B has the same meaning as defined above), and removing the hydroxy-protective group as the occasion demands.

The compounds represented by the above general formula (I) of the present invention can be also prepared by subjecting an amine compound represented by the general formula:

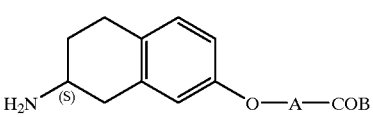
(VI)

(wherein A, B and the carbon atom marked with (S) have the same meanings as defined above) to N-alkylation using an alkylating agent represented by the above general formula (III), reducing the resulting compound in the usual way and removing the hydroxy-protective group.

Furthermore, the compounds represented by the above general formula (I) of the present invention can be prepared by allowing a mandelic acid derivative represented by the general formula:

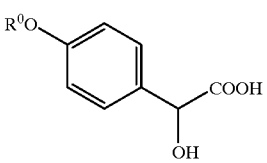
(VII)

(wherein $R^0$ has the same meaning as defined above) to react with an amine compound represented by the formula:

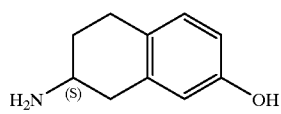

(VIII)

(wherein the carbon atom marked with (S) has the same meaning as defined above) in the presence of a condensing agent to give a compound represented by the general formula:

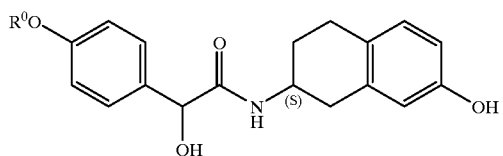

(IX)

(wherein $R^0$ and the carbon atom marked with (S) have the same meanings as defined above), reducing the resulting compound using a reagent such as a borane-dimethylsulfide complex to prepare a compound represented by the general formula:

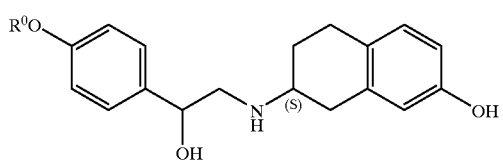

(X)

(wherein $R^0$ and the carbon atom marked with (S) have the same meanings as defined above), protecting the alcoholic hydroxy group and amino group with a reagent such as trifluoroacetic anhydride as the occasion demands, subjecting the resulting compound to O-alkylation using an alkylating agent represented by the general formula:

X—A—COB (XI)

(wherein A, B and X have the same meanings as defined above) and removing the protective group.

The amine compounds represented by the above general formulae (II) and (VIII) which are used as starting materials in the aforementioned production processes can be prepared according to a method described in the literature or analogous methods thereto (for example, *Eur. J. Med. Chem.*, No. 29, pp. 259–267 (1994); published Japanese patent application (Kokai) No. Hei 3–14548).

The compounds represented by the above general formula (III) which are used as starting materials in the aforementioned production processes can be prepared by subjecting a ketone compound represented by the general formula:

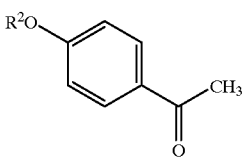

(XII)

(wherein $R^2$ represents a hydroxy-protective group suitable for this reaction) to halogenation using a halogenating agent according to a method described in the literature or analogous methods thereto (e.g., *Bull. Chem. Soc. Jpn.*, Vol. pp. 65, 295–297 (1992); *Synthesis*, No. 7, pp. 545–546 (1988); *Synthesis*, No. 12, pp. 1018–1020 (1982)), and converting the hydroxy-protective group of the resulting compound into other hydroxy-protective group as the occasion demands.

The amine compounds represented by the above general formula (VI) which are used as starting materials in the aforementioned production process can be prepared by subjecting a phenol compound represented by the general formula:

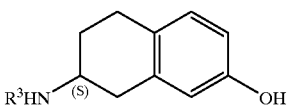

(XIII)

(wherein $R^3$ represents an amino-protective group; and the carbon atom marked with (S) has the same meaning as defined above) to O-alkylation using an alkylating agent represented by the above general formula (XI) and then removing the amino-protective group, or by protecting the amino group of an amine compound represented by the above general formula (II) using an appropriate reagent, converting the resulting compound into a free carboxylic acid or a reactive functional derivative thereof as the occasion demands, subjecting the resulting compound to amidation using an amine compound represented by the above general formula (V) in the presence or absence of a condensing agent and removing the amino-protective group.

Among the compounds represented by the above general formula (I) of the present invention, single isomers can be prepared, for example, by subjecting a diastereomer mixture obtained by the aforementioned process to fractional recrystallization in the usual way, or by allowing an optically active mandelic acid derivative represented by the general formula:

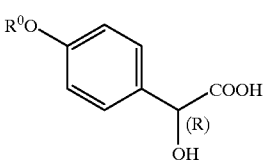

(XIV)

(wherein the carbon atom marked with (R) represents a carbon atom in (R) configuration; and $R^0$ has the same meaning as defined above) or an another optically active mandelic acid derivative represented by the general formula:

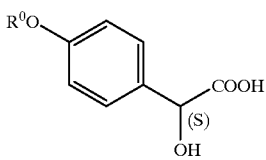

(XV)

(wherein R⁰ and the carbon atom marked with (S) have the same meanings as defined above) to react with an amine compound represented by the above formula (VIII) in the presence of a condensing agent to give a single isomer represented by the general formula:

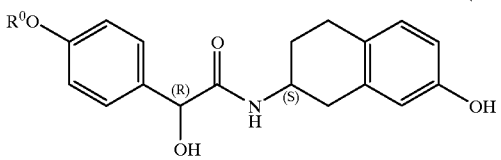

(XVI)

(wherein R⁰, the carbon atom marked with (R) and the carbon atom marked with (S) have the same meanings as defined above) or another single isomer represented by the general formula:

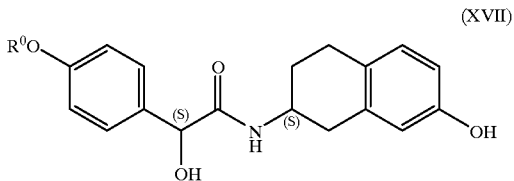

(XVII)

(wherein R⁰ and the carbon atoms marked with (S) have the same meanings as defined above), reducing the resulting isomer using a reagent such as borane-dimethylsulfide complex to prepare a compound represented by the general formula:

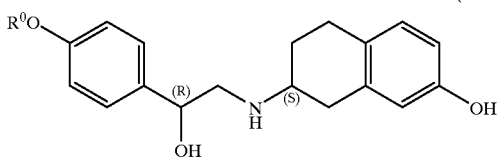

(XVIII)

(wherein R⁰, the carbon atom marked with (R) and the carbon atom marked with (S) have the same meanings as defined above) or a compound represented by the general formula:

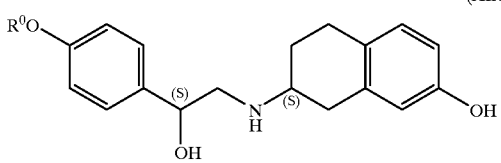

(XIX)

(wherein R⁰ and the carbon atoms marked with (S) have the same meanings as defined above), protecting the alcoholic hydroxy group and amino group using a reagent such as trifluoroacetic anhydride as the occasion demands, subjecting the resulting compound to O-alkylation using an alkylating agent represented by the above general formula (XI) and removing the protective group.

Among the compounds represented by the above general formula (I) of the present invention, single isomers can also be prepared by subjecting a diastereomer mixture obtained as an intermediate by the aforementioned process to column chromatography or fractional recrystallization to isolate the corresponding single isomer and then carrying out the same reaction using said single isomer.

The mandelic acid compounds represented by the above general formulae (VII), (XIV) and (XV) which are used as starting materials in the aforementioned production processes, for example, can be prepared by allowing a bromo compound represented by the general formula:

(XX)

(wherein R⁰ has the same meaning as defined above), which can be obtained according to a method described in the literature or analogous processes thereto, to react with diethyl oxalate, reducing the resulting phenylglyoxylic acid derivative using a reagent such as sodium borohydride, hydrolyzing the ester compound to give a mandelic acid derivative represented by the above general formula (VII), and subjecting the compound to optical resolution in the usual way using a resolving agent such as optically active 1-phenylethylamine as the occasion demands.

The compounds of the present invention obtained by the aforementioned production processes can be easily isolated and purified by conventional separation means such as fractional recrystallization, purification using column chromatography, solvent extraction and the like.

The phenylethanolaminotetralincarboxamide derivatives represented by the above general formula (I) of the present invention can be converted into their pharmaceutically acceptable salts in the usual way. Examples of the such salts include acid addition salts with mineral acids (e.g., hydrochloric acid, hydrobromic acid, hydroiodic acid, sulfuric acid, nitric acid, phosphoric acid and the like), acid addition salts with organic acids (e.g., formic acid, acetic acid, methanesulfonic acid, benzenesulfonic acid, p-toluenesulfonic acid, propionic acid, citric acid, succinic acid, tartaric acid, fumaric acid, butyric acid, oxalic acid, malonic acid, maleic acid, lactic acid, malic acid, carbonic acid, glutamic acid, aspartic acid and the like) and salts with inorganic bases such as a sodium salt and a potassium salt. The resulting salts have the same pharmacological activities as those of the free forms.

In addition, the compounds represented by the above general formula (I) of the present invention also include their hydrates and solvates with pharmaceutically acceptable solvents (e.g., ethanol).

The compounds represented by the above general formula (I) of the present invention exist in two isomer forms of (R) configuration and (S) configuration based on the asymmetric carbon atom having a hydroxy group. Either one of the isomers or a mixture thereof can be employed in the present invention.

When the in vitro test for measuring $\beta_2$-adrenergic receptor stimulating activity was carried out in the usual way using isolated pregnant rat uterus, the compounds represented by the above general formula (I) of the present invention showed an activity to relax 50% of the spontaneous contractions of rat myometrium (i.e., $EC_{50}$ value) at an approximate molar concentration of $5.0 \times 10^{-9}$ to $5.0 \times 10^{-6}$. For example, 2-[(2S)-2-[[(2R)-2-hydroxy-2-(4-hydroxyphenyl)-ethyl]amino]-1,2,3,4-tetrahydronaphthalen-7-yloxy]-N,N-dimethylacetamide showed the $EC_{50}$ value at a molar concentration of $1.5 \times 10^{-8}$. Thus, the compounds of the present invention have a markedly potent $\beta_2$-adrenergic receptor stimulating effect and therefore are remarkably useful as $\beta_2$-adrenergic receptor stimulating agents.

When the in vitro test for measuring $\beta_1$-adrenergic receptor stimulating activity was carried out in the usual way using isolated rat atrium, the compounds represented by the above general formula (I) of the present invention showed an activity to increase rat heart rate 20 beats per minute by the spontaneous motility of rat myocardium (i.e., $EC_{20}$ value) at an approximate molar concentration of $1.0 \times 10^{-6}$ or more. For example, 2-[(2S)-2-[[(2R)-2-hydroxy-2-(4-hydroxyphenyl)-ethyl]amino]-1,2,3,4-tetrahydronaphthalen-7-yloxy]-N,N-dimethylacetamide showed the $EC_{20}$ value at a molar concentration of $1.6 \times 10^{-6}$. Thus, the compounds of the present invention have a markedly weaker $\beta_1$-adrenergic receptor stimulating effect in comparison with the aforementioned $\beta_2$-adrenergic receptor stimulating effect.

As a consequence, the compounds of the present invention have a markedly potent $\beta_2$-adrenergic receptor stimulating effect with markedly high selectivity in comparison with a $\beta_1$-adrenergic receptor stimulating effect, so that these are extremely useful and selective $\beta_2$-adrenergic receptor stimulating agents of in which burdens on the heart are reduced due to suppression of side effects upon the heart (e.g., tachycardia) caused by a $\beta_1$-adrenergic receptor stimulating effect.

The present invention relates to a selective $\beta_2$-adrenergic receptor stimulating agent which is extremely useful as, for example, an agent for the prevention of threatened abortion, premature labor, a bronchodilator (an agent for the treatment and prevention of diseases associated with bronchiostenosis or airway obstruction), and an agent for pain remission or promoting stone removal in urolithiasis.

Also, the compounds represented by the above general formula (I) of the present invention are extremely stable compounds and therefore have excellent storage stability.

When the phenylethanolaminotetralincarboxamide derivatives represented by the above general formula (I) of the present invention and pharmaceutically acceptable salts thereof are employed in practical treatment, they are administered orally or parenterally in the form of appropriate pharmaceutical compositions such as tablets, powders, fine granules, granules, capsules, injections and the like. These pharmaceutical compositions can be formulated in accordance with conventional methods using conventional pharmaceutical carriers, excipients and other additives.

The dosage is appropriately decided depending on the sex, age, body weight, degree of symptoms and the like of each patient to be treated, which is approximately within the range of from 1 to 1,000 mg per day per adult human in the case of oral administration and approximately within the range of from 0.01 to 100 mg per day per adult human in the case of parenteral administration, and the daily dose can be divided into one to several doses per day.

EXAMPLES

The contents of the present invention are described further in detail with reference to the following Reference Examples, Examples and Test Examples, but the present invention is not limited thereto. All melting points of the compounds described in Reference Examples and Examples were uncorrected.

Reference Example 1

Ethyl 2-[(2S)-2-[[(2RS)-2-hydroxy-2-(4-hydroxyphenyl)-ethyl]amino]-1,2,3,4-tetrahydronaphthalen-7-yloxy]acetate 2-Bromo-4'-hydroxyacetophenone (860 mg) was dissolved in dichloromethane (20 ml), and 3,4-dihydro-2H-pyran (550 μl) and pyridinium p-toluenesulfonate (100 mg) were added to the solution at room temperature with stirring. After reaction for 17 hours, the reaction mixture was washed with water and dried over anhydrous magnesium sulfate, and the solvent was removed in vacuo. Purification of the residue by medium pressure liquid column chromatography on silica gel (eluent: hexane/ethyl acetate=10/1) gave 2-bromo-4'-((2RS)-2-tetrahydropyranyloxy)acetophenone (1.01 g) having a melting point of 102–104° C.

IR (KBr): 1687 $cm^{-1}$ $^1$H-NMR (CDCl$_3$) δ ppm: 1.50–2.10 (6H, m), 3.55–3.65 (1H, m), 3.75–3.90 (1H, m), 4.41 (2H, s), 5.54 (1H, t, J=3.1 Hz), 7.11 (2H, d, J=9.0H z), 7.96 (2H, d, J=9.0 Hz)

Ethyl (S)-(2-amino-1,2,3,4-tetrahydronaphthalen-7-yloxy)acetate (1.14 g) was dissolved in N,N-dimethylformamide (15 ml), and 2-bromo-4'-((2RS)-2-tetrahydropyranyloxy)-acetophenone (600 mg) was added to the solution under ice-cooling with stirring, followed by reaction at room temperature for an hour. Sodium borohydride (380 mg) and ethanol (10 ml) were added to the reaction mixture under ice-cooling with stirring. After reaction for an hour, the reaction mixture was poured into ice-water and extracted with ethyl acetate. The extract was washed with water and dried over anhydrous magnesium sulfate, and the solvent was removed in vacuo. The resulting residue was dissolved in tetrahydrofuran (20 ml), triethanolamine (2 ml) was added to the solution and the mixture was heated under reflux for 17 hours. After cooling, water was poured into the reaction mixture and the resulting mixture was extracted with ethyl acetate. The extract was washed with water and dried over anhydrous magnesium sulfate, and the solvent was removed in vacuo. Purification of the residue by medium pressure liquid column chromatography on silica gel (eluent: ethyl acetate) gave ethyl 2-[(2S)-2-[[(2RS)-2-hydroxy-2-[4-((2RS)-2-tetrahydropyranyloxy)phenyl]ethyl]amino]-1,2,3,4-tetrahydronaphthalen-7-yloxy]acetate (780 mg) as an oil.

IR (neat): 3304, 1760 $cm^{-1}$ $^1$H-NMR (CDCl$_3$) δ ppm: 1.15–1.65 (8H, m), 1.80–2.10 (4H, m), 2.50–3.05 (7H, m), 3.55–3.65 (1H, m), 3.85–3.95 (1H, m), 4.20–4.30 (2H, m), 4.55–4.70 (3H, m), 5.41 (1H, t, J=3.2 Hz), 6.61 (1H, s), 6.69 (1H, dd, J=8.4, 2.7 Hz), 6.95–7.10 (3H, m), 7.25–7.35 (2H, m)

Ethyl 2-[(2S)-2-[[(2RS)-2-hydroxy-2-[4-((2RS)-2-tetrahydropyranyloxy)phenyl]ethyl]amino]-1,2,3,4-tetrahydronaphthalen-7-yloxy]acetate (780 mg) was dissolved in ethanol (20 ml), and 1N hydrochloric acid (34 ml) was added to the solution under ice-cooling with stirring. After reaction for an hour, the reaction mixture was neutralized with a saturated aqueous sodium bicarbonate solution and extracted with ethyl acetate. The extract was washed with water and dried over anhydrous magnesium sulfate, and the solvent was removed in vacuo. Purification of the residue by medium pressure liquid column chromatography on silica gel (eluent: ethyl acetate) gave ethyl 2-[(2S)-2-[[(2RS)-2-hydroxy-2-(4-hydroxyphenyl)ethyl]-amino]-1,2,3,4-tetrahydronaphthalen-7-yloxy]acetate (238 mg) as an amorphous.

IR (film): 3294, 1754 cm$^{-1}$ $^1$H-NMR (CDCl$_3$) δ ppm: 1.15–1.25 (3H, m), 1.50–1.65 (1H, m), 1.95–2.10 (1H, m), 2.45–2.60 (1H, m), 2.65–3.05 (6H, m), 3.73 (3H, br), 4.20–4.30 (2H, m), 4.50–4.70 (3H, m), 6.50–6.60 (1H, m), 6.67 (1H, dd, J=8.4, 2.6 Hz), 6.75 (2H, d, J=8.4 Hz), 6.97 (1H, d, J=8.4 Hz), 7.17 (2H, d, J=8.4 Hz)

Reference Example 2

4-[(2S)-2-[[(2RS)-2-(4-Benzyloxyphenyl)-2-hydroxy-ethyl]amino]-1,2,3,4-tetrahydronaphthalen-7-yloxy]-N,N-dimethylbutyramide (S)-2-(tert-Butoxycarbonylamino)-7-hydroxytetralin (400 mg) was dissolved in N,N-dimethylformamide (8 ml), and cesium carbonate (3.16 g) and ethyl 4-bromobutyrate (650 µl) were added to the solution at room temperature with stirring. After reaction for 1.5 hours, water was poured into the reaction mixture and the resulting mixture was extracted with ethyl acetate. The extract was washed with water and dried over anhydrous magnesium sulfate, and the solvent was removed in vacuo. Purification of the residue by medium pressure liquid column chromatography on silica gel (eluent: hexane/ethyl acetate=1/1) gave ethyl (S)-4-[2-(tert-butoxycarbonyl-amino)-1,2,3,4-tetrahydronaphthalen-7-yloxy]butyrate (488 mg) having a melting point of 96–98° C.

IR (KBr): 3360, 1723, 1680 cm$^{-1}$ $^1$H-NMR (CDCl$_3$) δ ppm: 1.26 (3H, t, J=7.1 Hz), 1.45 (9H, s), 1.65–1.80 (1H, m), 2.00–2.15 (3H, m), 2.50 (2H, t, J=7.3 Hz), 2.59 (1H, dd, J=16.5, 7.9 Hz), 2.75–2.85 (2H, m), 3.07 (1H, dd, J=16.5, 4.6 Hz), 3.90–4.05 (3H, m), 4.14 (2H, q, J=7.1 Hz), 4.50–4.65 (1H, m), 6.58 (1H, d, J=2.6 Hz), 6.68 (1H, dd, J=8.4, 2.6 Hz), 6.99 (1H, d, J=8.4 Hz)

Optical rotation: [α]$_D^{25}$=−50.7° (c=1.03, MeOH)

Ethyl (s)-4-[2-(tert-butoxycarbonylamino)-1,2,3,4-tetrahydronaphthalen-7-yloxy]butyrate (988 mg) was dissolved in a mixed solvent of methanol (15 ml) and ethanol (15 ml), and 2N aqueous sodium hydroxide solution (3.0 ml) was added to the solution at room temperature with stirring. After reaction for 2 hours, the reaction mixture was concentrated in vacuo. To the resulting residue was added 10% aqueous citric acid solution, and the mixture was extracted with ethyl acetate. The extract was washed with brine and dried over anhydrous magnesium sulfate. The solvent was removed in vacuo to give (S)-4-[2-(tert-butoxycarbonylamino)-1,2,3,4-tetrahydronaphthalen-7-yloxy]butyric acid (914 mg) having a melting point of 150–153° C.

IR (KBr): 3452, 3365, 1691 cm$^{-1}$ $^1$H-NMR (CDCl$_3$) δ ppm: 1.45 (9H, s), 1.65–1.80 (1H, m), 2.00–2.20 (3H, m), 2.55–2.70 (3H, m), 2.75–2.85 (2H, m), 3.00–3.15 (1H, m), 3.90–4.10 (3H, m), 4.55–4.70 (1H, m), 6.58 (1H, d, J=2.6 Hz), 6.68 (1H, dd, J=8.4, 2.6 Hz), 6.99 (1H, d, J=8.4 Hz)

Optical rotation: [α]$_D^{25}$=−53.5° (c=0.52, MeOH)

(S)-4-[2-(tert-Butoxycarbonylamino)-1,2,3,4-tetrahydronaphthalen-7-yloxy]butyric acid (399 mg) was dissolved in tetrahydrofuran (5 ml), and N,N'-carbonyldiimidazole (204 mg) was added to the solution under ice-cooling with stirring. After reaction for 2 hours, a solution of dimethylamine (1.40 g) in tetrahydrofuran (2 ml) was added to the reaction mixture under ice-cooling with stirring. After reaction for 45 minutes and then at room temperature for 45 minutes, the reaction mixture was concentrated in vacuo. Water was added to the resulting residue and the mixture was extracted with diethyl ether. The extract was washed with 10% aqueous citric acid solution, water, a saturated aqueous sodium bicarbonate solution and water successively, and dried over anhydrous magnesium sulfate. The solvent was removed in vacuo to give (S)-4-[2-(tert-butoxycarbonylamino)-1,2,3,4-tetrahydronaphthalen-7-yloxy]-N,N-dimethylbutyramide (396 mg) having a melting point of 97–101° C.

IR (KBr): 3325, 1709, 1624 cm$^{-1}$ $^1$H-NMR (CDCl$_3$) δ ppm: 1.45 (9H, s), 1.65–1.80 (1H, m), 2.00–2.15 (3H, m), 2.51 (2H, t, J=7.2 Hz), 2.59 (1H, dd, J=16.5, 8.1 Hz), 2.75–2.85 (2H, m), 2.95 (3H, s), 3.00–3.10 (4H, m), 3.90–4.00 (3H, m), 4.58 (1H, br s), 6.59 (1H, d, J=2.6 Hz), 6.69 (1H, dd, J=8.4, 2.6 Hz), 6.98 (1H, d, J=8.4 Hz)

Optical rotation: [α]$_D^{25}$=−50.0° (c=0.50, MeOH)

(S)-4-[2-(tert-Butoxycarbonylamino)-1,2,3,4-tetrahydronaphthalen-7-yloxy]-N,N-dimethylbutyramide (396 mg) was dissolved in dichloromethane (5 ml), a solution of trifluoroacetic acid (5 ml) in dichloromethane (5 ml) was added to the solution under ice-cooling with stirring, and the mixture was still stirred for 15 minutes. After reaction at room temperature for 15 minutes, the reaction mixture was concentrated in vacuo. Dichloromethane, water and sodium bicarbonate were added to the resulting residue and the mixture was stirred at room temperature for 30 minutes. The organic layer was separated and dried over anhydrous magnesium sulfate. The solvent was removed in vacuo to give (S)-4-(2-amino-1,2,3,4-tetrahydronaphthalen-7-yloxy)-N,N-dimethylbutyramide (263 mg) as an oil.

IR (neat): 3404, 1618 cm$^{-1}$ $^1$H-NMR (CDCl$_3$) δ ppm: 1.75–1.90 (1H, m), 2.00–2.25 (3H, m), 2.45–2.55 (2H, m), 2.65–2.90 (3H, m), 2.94 (3H, s), 3.00 (3H, s), 3.05–3.20 (1H, m), 3.30–3.50 (1H, m), 3.96 (2H, t, J=5.9 Hz), 5.89 (2H, br s), 6.60 (1H, d, J=2.3 Hz), 6.68 (1H, dd, J=8.4, 2.3 Hz), 6.96 (1H, d, J=8.4 Hz)

Optical rotation: [α]$_D^{25}$=−46.2° (c=0.45, MeOH)

(S)-4-(2-Amino-1,2,3,4-tetrahydronaphthalen-7-yloxy)-N,N-dimethylbutyramide (196 mg) and triethylamine (270 µl) were dissolved in N,N-dimethylformamide (3 ml), and a solution of 4'-benzyloxy-2-bromoacetophenone (195 mg) in N,N-dimethylformamide (2 ml) was added to the solution under ice-cooling with stirring. After reaction for 15 minutes, sodium borohydride (240 mg) and ethanol (3 ml) were added to the reaction mixture under ice-cooling with stirring. After reaction for 2 hours, the reaction mixture was poured into ice-water, and the resulting mixture was extracted with ethyl acetate. The extract was washed with water and dried over anhydrous magnesium sulfate, and the solvent was removed in vacuo. To the resulting residue was added a solution of triethanolamine (200 mg) in tetrahydrofuran (5 ml), and the mixture was heated under reflux for 16 hours. After cooling, water was poured into the reaction mixture and the resulting mixture was extracted with ethyl acetate. The extract was washed with water and dried over anhydrous magnesium sulfate, and the solvent was removed in vacuo. Purification of the residue by medium pressure liquid column chromatography on silica gel (eluent: ethyl acetate/ethanol=6/1) gave 4-[(2S)-2-[[(2RS)-2-(4-benzyloxyphenyl)-2-hydroxyethyl]amino]-1,2,3,4-tetrahydronaphthalen-7-yloxy]-N,N-dimethylbutyramide (85 mg) as an amorphous.

IR (film): 3348, 1639 cm$^{-1}$ $^1$H-NMR (CDCl$_3$) δ ppm: 1.55–1.65 (1H, m), 1.80–2.30 (5H, m), 2.45–2.85 (6H, m), 2.90–3.10 (9H, m), 3.95–4.05

(2H, m), 4.67 (1H, dd, J=9.1, 3.3 Hz), 5.07 (2H, s), 6.60 (1H, s), 6.68 (1H, dd, J=8.4, 2.7 Hz), 6.90–7.05 (3H, m), 7.20–7.50 (7H, m)

Reference Example 3

2-[(2S)-2-[[(2R)-2-(4-Benzyloxyphenyl)-2-hydroxyethyl]-amino]-1,2,3,4-tetrahydronaphthalen-7-yloxy]-N,N-dimethylacetamide (R)-4-Hydroxymandelic acid (2.02 g) was dissolved in N,N-dimethylformamide (24 ml), and benzyl bromide (3.57 ml) and potassium carbonate (3.65 g) were added to the solution at room temperature with stirring. After reaction for 12 hours, ice-water was poured into the reaction mixture and the resulting precipitates were collected by filtration. The precipitates were suspended in methanol (24 ml) and 1N aqueous sodium hydroxide solution (12 ml) was added to the suspension under ice-cooling with stirring. After reaction at room temperature for 2 hours, 1N hydrochloric acid (12 ml) was added to the reaction mixture under ice-cooling with stirring. Collection by filtration of the resulting precipitates gave (R)-4-benzyloxymandelic acid (2.43 g) having a melting point of 161–163° C.

IR (KBr): 3439, 1733 cm$^{-1}$ $^1$H-NMR (DMSO-d$_6$) δ ppm: 4.96 (1H, s), 5.10 (2H, s), 5.75 (1H, br), 6.95–7.05 (2H, m), 7.25–7.50 (7H, m), 12.52 (1H, br)

Optical rotation: $[\alpha]_D^{25}$=–100.5° (c=1.00, MeOH)

(R)-4-Benzyloxymandelic acid (2.43 g), (S)-2-amino-7-hydroxytetralin hydrobromide (2.87 g) and triethylamine (2.88 ml) were dissolved in dichloromethane (38 ml), and benzotriazol-1-yloxytris(dimethylamino)phosphonium hexafluorophosphate (4.58 g) was added to the solution at room temperature with stirring. After reaction for 15 hours, ethyl acetate was added to the reaction mixture. The resulting mixture was washed with water, 1N hydrochloric acid, a saturated aqueous sodium bicarbonate solution and brine successively, dried over anhydrous magnesium sulfate, and the solvent was removed in vacuo. Purification of the residue by medium pressure liquid column chromatography on silica gel (eluent: chloroform/ethyl acetate=1/1) and following recrystallization from ethyl acetate-hexane gave (2R)-2-(4-benzyloxyphenyl)-2-hydroxy-N-((2S)-7-hydroxy-1,2,3,4-tetrahydronaphthalen-2-yl)acetamide (3.48 g) having a melting point of 137–139° C.

IR (KBr): 3374, 1630 cm$^{-1}$ $^1$H-NMR (CDCl$_3$) δ ppm: 1.60–1.75 (1H, m), 1.90–2.00 (1H, m), 2.53 (1H, dd, J=16.3, 8.3 Hz), 2.60–2.80 (2H, m), 2.97 (1H, dd, J=16.3, 5.0 Hz), 3.43 (1H, br), 4.15–4.30 (1H, m), 4.97 (1H, s), 5.03 (2H, s), 5.70 (1H, br), 6.34 (1H, d, J=8.1 Hz), 6.43 (1H, d, J=2.6 Hz), 6.59 (1H, dd, J=8.3, 2.6 Hz), 6.88 (1H, d, J=8.3 Hz), 6.93 (2H, d, J=8.7 Hz), 7.20–7.50 (7H, m)

Optical rotation: $[\alpha]_D^{25}$=–89.4° (c=1.06, MeOH)

(2R)-2-(4-Benzyloxyphenyl)-2-hydroxy-N-((2S)-7-hydroxy-1,2,3,4-tetrahydronaphthalen-2-yl)acetamide (605 mg) was dissolved in tetrahydrofuran (7.5 ml), and 2M borane-dimethyl-sulfide complex in tetrahydrofuran (2.25 ml) was added to the solution at room temperature with stirring. After the mixture was heated under reflux for 3 hours, a solution of triethanolamine (1.12 g) in tetrahydrofuran (2.5 ml) was added to the reaction mixture and the mixture was heated under reflux for 15 hours. After cooling, water was poured into the reaction mixture and the resulting mixture was extracted with ethyl acetate. The extract was washed with water and dried over anhydrous magnesium sulfate, and the solvent was removed in vacuo. Recrystallization of the residue from ethyl acetate gave (1R)-1-(4-benzyloxyphenyl)-2-[((2S)-7-hydroxy-1,2,3,4-tetrahydronaphthalen-2-yl)-amino]ethanol (350 mg) having a melting point of 132–134° C.

IR (KBr): 3250 cm$^{-1}$ $^1$H-NMR (CDCl$_3$) δ ppm: 1.20–2.10 (2H, m), 2.50–3.05 (7H, m), 3.50 (1H, br), 4.60–4.70 (1H, m), 5.06 (2H, s), 6.50–6.55 (1H, m), 6.60 (1H, dd, J=8.2, 2.7 Hz), 6.90–7.00 (3H, m), 7.25–7.50 (7H, m)

Optical rotation: $[\alpha]_D^{25}$=–63.1° (c=0.98, MeOH)

To a stirred suspension of (1R)-1-(4-benzyloxyphenyl)-2-[((2S)-7-hydroxy-1,2,3,4-tetrahydronaphthalen-2-yl)amino]-ethanol (350 mg) and N,N-diisopropylethylamine (0.78 ml) in dichloromethane (3.6 ml) was added trifluoroacetic anhydride (0.38 ml) at –15° C. After reaction for 30 minutes, the reaction mixture was washed with water and dried over anhydrous magnesium sulfate, and the solvent was removed in vacuo. The resulting residue was dissolved in N,N-dimethylformamide (4.5 ml), and 2-bromo-N,N-dimethylacetamide (0.11 ml), cesium carbonate (880 mg) and molecular sieves 4A powder (350 mg) were added to the solution. After the mixture was stirred at room temperature for 2 hours, diethylamine (0.11 ml) was added to the reaction mixture. After reaction at room temperature for 20 minutes, water (3.5 ml) and methanol (3.5 ml) were added to the reaction mixture under ice-cooling and the mixture was stirred at room temperature for 1.5 hours. Brine was poured into the reaction mixture and the resulting mixture was extracted with ethyl acetate. The extract was washed with brine and dried over anhydrous magnesium sulfate, and the solvent was removed in vacuo. Purification of the residue by medium pressure liquid column chromatography on aminopropyl silica gel (eluent: chloroform/methanol=50/1) gave 2-[(2S)-2-[[(2R)-2-(4-benzyloxyphenyl)-2-hydroxy-ethyl]amino]-1,2,3,4-tetrahydronaphthalen-7-yloxy]-N,N-dimethylacetamide (283 mg) as an amorphous.

IR (KBr): 3430, 1651 cm$^{-1}$ $^1$H-NMR (CDCl$_3$) δ ppm: 1.35–1.70 (2H, m), 2.00–2.10 (1H, m), 2.50–3.15 (13H, m), 3.50 (1H, br), 4.60–4.70 (3H, m), 5.07 (2H, s), 6.65 (1H, d, J=2.5 Hz), 6.73 (1H, dd, J=8.4, 2.5 Hz), 6.90–7.05 (3H, m), 7.25–7.50 (7H, m)

Optical rotation: $([\alpha]_D^{25}$=–61.0° (c=0.62, MeOH)

Reference Example 4

The following compounds were prepared according to a similar reaction and treatment to that described in Reference Example 3 using 1-bromoacetylpiperidine or 4-bromoacetylmorpholine instead of 2-bromo-N,N-dimethylacetamide.

1-[2-[(2S)-2-[[(2R)-2-(4-Benzyloxyphenyl)-2-hydroxyethyl]-amino]-1,2,3,4-tetrahydronaphthalen-7-yloxy]acetyl]piperidine amorphous IR (KBr): 3420, 1645 cm$^{-1}$ $^1$H-NMR (CDCl$_3$) δ ppm: 1.50–1.70 (7H, m), 2.00–2.10 (1H, m), 2.50–2.65 (1H, m), 2.70–2.85 (3H, m), 2.95–3.10 (3H, m), 3.45–3.60 (4H, m), 4.63 (2H, s), 4.66 (1H, dd, J=9.0, 3.5 Hz), 5.07 (2H, s), 6.65 (1H, d, J=2.7 Hz), 6.73 (1H, dd, J=8.4, 2.7 Hz), 6.95–7.05 (3H, m), 7.25–7.50 (7H, m)

Optical rotation: $[\alpha]_D^{25}$=–53.0° (c=0.54, MeOH)

4-[2-[(2S)-2-[[(2R)-2-(4-Benzyloxyphenyl)-2-hydroxyethyl]-amino]-1,2,3,4-tetrahydronaphthalen-7-yloxy]acetyl]morpholine amorphous IR (film): 3365, 1653 cm$^{-1}$ $^1$H-NMR (CDCl$_3$) δ ppm: 1.55–1.70 (1H, m), 2.00–2.10 (1H, m), 2.50–3.10 (7H, m), 3.55–3.75 (9H, m), 4.60–4.70 (3H, m), 5.06 (2H, s), 6.64 (1H, d, J=2.6 Hz), 6.72 (1H, dd, J=8.4, 2.6 Hz), 6.96 (2H, d, J=8.6 Hz), 7.00 (1H, d, J=8.4 Hz), 7.25–7.50 (7H, m)

Optical rotation: [α]$_D^{25}$=−49.8° (c=0.59, MeOH)

Reference Example 5

2-[(2S)-2-[[(2S)-2-(4-Benzyloxyphenyl)-2-hydroxyethyl]-amino]-1,2,3,4-tetrahydronaphthalen-7-yloxy]-N,N-dimethylacetamide 4-Benzyloxymandelic acid (40.8 g) was dissolved in methanol (405 ml) and ethyl acetate (405 ml), and a solution of (S)-1-phenylethylamine (20.4 ml) in methanol (200 ml) and ethyl acetate (200 ml) was added to the solution. After the mixture was allowed to stand at room temperature, the resulting precipitates (37.9 g) were obtained. Recrystallization of the precipitates from methanol (926 ml) gave a salt of (S)-1-phenylethylamine and (S)-4-benzyloxymandelic acid (24.8 g) having a melting point of 174–180° C.

IR (KBr): 3301, 3036, 1609 cm$^{-1}$ $^1$H-NMR (DMSO-d$_6$) δ ppm: 1.42 (3H, d, J=6.7 Hz), 4.27 (1H, q, J=6.7 Hz), 4.50 (1H, s), 5.07 (2H, s), 6.85–6.95 (2H, m), 7.20–8.00 (14H, m)

Optical rotation: [α]$_D^{25}$=+36.2° (c=0.50, MeOH)

A salt of (S)-1-phenylethylamine and (S)-4-benzyloxymandelic acid (1.0 g) was suspended in a mixed solvent of ethyl acetate (20 ml) and water (20 ml), and 1N hydrochloric acid (3.0 ml) was added to the solution under ice-cooling. After the mixture was stirred for 30 minutes, the organic layer was separated, washed with water and dried over anhydrous magnesium sulfate. The solvent was removed in vacuo to give (S)-4-benzyloxymandelic acid (595 mg) having a melting point of 158–162° C.

IR (KBr): 3440, 1734 cm$^{-1}$ $^1$H-NMR (DMSO-d$_6$) δ ppm: 4.95 (1H, s), 5.09 (2H, s), 5.70 (1H, br), 6.90–7.00 (2H, m), 7.25–7.50 (7H, m), 12.30 (1H, br)

Optical rotation: [α]$_D^{25}$=+99.9° (c=1.00, MeOH)

(S)-4-Benzyloxymandelic acid (1.80 g), (S)-2-amino-7-hydroxytetralin hydrobromide (1.87 g) and benzotriazol-1-yloxy-tris(dimethylamino)phosphonium hexafluorophosphate (3.39 g) were dissolved in N,N-dimethylformamide (21 ml), and triethylamine (2.03 ml) was added to the solution under ice-cooling with stirring. After reaction at room temperature for an hour, diethyl ether and water were added to the reaction mixture. Collection by filtration of the resulting precipitates gave (2S)-2-(4-benzyloxyphenyl)-2-hydroxy-N-((2S)-7-hydroxy-1,2,3,4-tetrahydronaphthalen-2-yl)acetamide (2.64 g) as powders.

IR (KBr): 3487, 3402, 1652 cm$^{-1}$ $^1$H-NMR (CDCl$_3$) δ ppm: 1.65–1.80 (1H, m), 1.95–2.10 (1H, m), 2.53 (1H, dd, J=16.3, 8.6 Hz), 2.65–2.85 (2H, m), 3.00 (1H, dd, J=16.3, 5.1 Hz), 4.15–4.20 (1H, m), 4.99 (1H, s), 5.06 (2H, s), 6.32 (1H, d, J=8.0 Hz), 6.48 (1H, d, J=2.6 Hz), 6.62 (1H, dd, J=8.3, 2.6 Hz), 6.85–7.00 (3H, m), 7.20–7.50 (7H, m)

Optical rotation: [α]$_D^{25}$=−6.8° (c=1.00, MeOH)

(2S)-2-(4-Benzyloxyphenyl)-2-hydroxy-N-((2S)-7-hydroxy-1,2,3,4-tetrahydronaphthalen-2-yl)acetamide (2.50 g) was dissolved in tetrahydrofuran (31 ml), and borane-dimethyl-sulfide complex (1.76 ml) was added to the solution. After the mixture was heated under reflux for 4 hours, a solution of triethanolamine (4.62 g) in tetrahydrofuran (4.6 ml) was added to the reaction mixture and the mixture was heated under reflux for 11 hours. After cooling, water was poured into the reaction mixture and the resulting mixture was extracted with ethyl acetate. The extract was washed with water and dried over anhydrous magnesium sulfate, and the solvent was removed in vacuo. Purification of the residue by medium pressure liquid column chromatography on silica gel (eluent: ethyl acetate/ethanol=7/1) gave (1S)-1-(4-benzyloxy-phenyl)-2-[((2S)-7-hydroxy-1,2,3,4-tetrahydronaphthalen-2-yl)amino]ethanol (1.63 g) as an amorphous.

IR (KBr): 3290 cm$^{-1}$ $^1$H-NMR (CDCl$_3$) δ ppm: 1.55–1.70 (1H, m), 1.95–2.10 (1H, m), 2.50–3.05 (7H, m), 3.40 (2H, br), 4.67 (1H, dd, J=9.1, 3.5 Hz), 5.06 (2H, s), 6.50 (1H, d, J=2.6 Hz), 6.60 (1H, dd, J=8.2, 2.6 Hz), 6.93 (1H, d, J=8.2 Hz), 6.96 (2H, d, J=8.7 Hz), 7.20–7.50 (7H, m)

Optical rotation: [α]$_D^{25}$=−11.9° (c=1.00, CHCl$_3$)

To a stirred suspension of (1S)-1-(4-benzyloxyphenyl)-2-[((2S)-7-hydroxy-1,2,3,4-tetrahydronaphthalen-2-yl)amino]-ethanol (1.30 g) and N,N-diisopropylethylamine (2.91 ml) in dichloromethane (16.7 ml) was added trifluoroacetic anhydride (1.41 ml) at −15° C. After reaction for 20 minutes, water was poured into the reaction mixture and the resulting mixture was extracted with dichloromethane. The extract was washed with water and brine, dried over anhydrous magnesium sulfate, and the solvent was removed in vacuo. The resulting residue was dissolved in N,N-dimethylformamide (8.6 ml), and 2-bromo-N,N-dimethylacetamide (571 mg), cesium carbonate (2.52 g) and molecular sieves 4A powder (860 mg) were added to the solution. After reaction at room temperature for 2.5 hours, water and methanol were added to the reaction mixture under ice-cooling and the resulting mixture was stirred at room temperature for 12 hours. The insoluble material was filtered off and the filtrate was concentrated in vacuo. The resulting residue was dissolved in ethyl acetate, washed with water and brine, and dried over anhydrous magnesium sulfate, and the solvent was removed in vacuo. Recrystallization of the residue from diethyl ether gave 2-[(2S)-2-[[(2S)-2-(4-benzyloxyphenyl)-2-hydroxyethyl]amino]-1,2,3,4-tetrahydronaphthalen-7-yloxy]-N,N-dimethylacetamide (437 mg) having a melting point of 103–106° C.

IR (KBr): 3438, 1672, 1653 cm$^{-1}$ $^1$H-NMR (CDCl$_3$) δ ppm: 1.50–1.70 (1H, m), 2.00–2.15 (1H, m), 2.55–3.10 (13H, m), 4.60–4.70 (3H, m), 5.07 (2H, s), 6.64 (1H, d, J=2.8 Hz), 6.74 (1H, dd, J=8.4, 2.8 Hz), 6.97 (2H, d, J=8.8 Hz), 6.99 (1H, d, J=8.4 Hz), 7.20–7.50 (7H, m)

Optical rotation: [α]$_D^{25}$=−14.2° (c=1.00, CHCl$_3$)

Reference Example 6

The following compounds were prepared according to a similar reaction and treatment to that described in Reference Example 5 using 1-bromoacetylpiperidine or 4-bromoacetyl-morpholine instead of 2-bromo-N,N-dimethylacetamide.

1-[2-[(2S)-2-[[(2S)-2-(4-Benzyloxyphenyl)-2-hydroxyethyl]-amino]-1,2,3,4-tetrahydronaphthalen-7-yloxy]acetyl]piperidine oil IR (neat): 3304, 1638 cm$^{-1}$ $^1$H-NMR (CDCl$_3$) δ ppm : 1.50–1.70 (7H, m), 2.00–2.15 (1H, m), 2.50–3.05 (7H, m), 3.40–3.60 (4H, m), 4.60–4.70 (3H, m), 5.07 (2H, s), 6.64 (1H, d, J=2.7 Hz), 6.73 (1H, dd, J=8.4, 2.7 Hz), 6.90–7.05 (3H, m), 7.25–7.60 (7H, m)

Optical rotation: [α]$_D^{25}$=−12.1° (c=1.00, CHCl$_3$)

4-[2-[(2S)-2-[[(2S)-2-(4-Benzyloxyphenyl)-2-hydroxyethyl]-amino]-1,2,3,4-tetrahydronaphthalen-7-yloxy]acetyl]morpholine amorphous IR (KBr): 3438, 1651 cm$^{-1}$ $^1$H-NMR (CDC$_{l3}$) δ ppm: 1.50–1.70 (1H, m), 2.00–2.10 (1H, m), 2.50–3.10 (7H, m), 3.55–3.75 (9H, m), 4.60–4.70 (3H, m), 5.07 (2H, s), 6.64 (1H, d, J=2.7 Hz), 6.72 (1H, dd, J=8.4, 2.7 Hz), 6.97 (2H, d, J=8.7 Hz), 6.98 (1H, d, J=8.4 Hz), 7.25–7.50 (7H, m)

Optical rotation: $[\alpha]_D^{25}$=−26.3° (c=0.50, MeOH)

Example 1

2-[(2S)-2-[[(2RS)-2-Hydroxy-2-(4-hydroxyphenyl) ethyl]-amino]-1,2,3,4-tetrahydronaphthalen-7-yloxy]-N,N-dimethylacetamide Ethyl 2-[(2S)-2-[[(2RS)-2-hydroxy-2-(4-hydroxyphenyl)-ethyl]amino]-1,2,3,4-tetrahydronaphthalen-7-yloxy]acetate (250 mg) was dissolved in tetrahydrofuran (5 ml), and dimethylamine (1 ml) was added to the solution under ice-cooling. After reaction in sealed tube at 60° C. for 60 hours, the reaction mixture was concentrated in vacuo. Purification of the residue by medium pressure liquid column chromatography on aminopropyl silica gel (eluent: ethyl acetate/ethanol=10/1) gave 2-[(2S)-2-[[(2RS)-2-hydroxy-2-(4-hydroxyphenyl)-ethyl]amino]-1,2,3,4-tetrahydronaphthalen-7-yloxy]-N,N-dimethylacetamide (189 mg) as an amorphous.

IR (KBr): 3290, 1651 cm$^{-1}$ $^1$H-NMR (DMSO-d$_6$) δ ppm: 1.35–1.70 (2H, m), 1.80–2.00 (1H, m), 2.35–3.05 (13H, m), 4.45–4.55 (1H, m), 4.65–4.75 (2H, m), 5.06 (1H, br s), 6.55–6.75 (4H, m), 6.93 (1H, d, J=8.4 Hz), 7.14 (2H, d, J=8.3 Hz), 9.19 (1H, br s)

Example 2

The following compounds were prepared according to a similar reaction and treatment to that described in Example 1 using piperidine, morpholine or pyrrolidine instead of dimethylamine.

1-[2-[(2S)-2-[[(2RS)-2-Hydroxy-2-(4-hydroxyphenyl) ethyl]-amino]-1,2,3,4-tetrahydronaphthalen-7-yloxy]acetyl] piperidine amorphous IR (KBr): 3397, 1638 cm$^{-1}$ $^1$H-NMR (CDCl$_3$) δ ppm: 1.40–1.70 (7H, m), 2.00–2.10 (1H, m), 2.45–3.10 (7H, m), 3.40–3.70 (4H, m), 4.60–4.70 (3H, m), 6.62 (1H, d, J=2.6 Hz), 6.65–6.85 (3H, m), 6.97 (1H, d, J=8.4 Hz), 7.20–7.25 (2H, m)

4-[2-[(2S)-2-[[(2RS)-2-Hydroxy-2-(4-hydroxyphenyl) ethyl]-amino]-1,2,3,4-tetrahydronaphthalen-7-yloxy]acetyl] morpholine amorphous IR (Ksr): 3402, 1651 cm$^{-1}$ $^1$H-NMR (CDCl$_3$) δ ppm: 1.50–1.65 (1H, m), 1.95–2.10 (1H, m), 2.40–2.55 (1H, m), 2.60–3.00 (6H, m), 3.55–3.75 (8H, m), 4.60–4.70 (3H, m), 6.55–6.65 (1H, m), 6.69 (1H, dd, J=8.4, 2.7 Hz), 6.79 (2H, d, J=8.5 Hz), 6.97 (1H, d, J=8.4 Hz), 7.19 (2H, d, J=8.5 Hz)

1-[2-[(2S) -2-[[(2RS) -2-Hydroxy-2-(4-hydroxyphenyl) ethyl]-amino]-1,2,3,4-tetrahydronaphthalen-7-yloxy]acetyl] pyrrolidine amorphous IR (KBr): 3403, 1643 cm$^{-1}$ $^1$H-NMR (CDCl$_3$) δ ppm: 1.45–1.65 (1H, m), 1.70–2.05 (6H, m), 2.10–3.00 (9H, m), 3.45–3.55 (4H, m), 4.55–4.70 (3H, m), 6.58 (1H, dd, J=8.2, 2.7 Hz), 6.65–6.75 (1H, m), 6.80 (2H, d, J=8.4 Hz), 6.96 (1H, d, J=8.2 Hz), 7.18 (2H, d, J=8.4 Hz)

Example 3

2-[(2S)-2-[[(2R)-2-Hydroxy-2-(4-hydroxyphenyl)ethyl]-amino]-1,2,3,4-tetrahydronaphthalen-7-yloxy]-N,N-dimethylacetamide 2-[(2S)-2-[[(2R)-2-(4-Benzyloxyphenyl)-2-hydroxyethyl]-amino]-1,2,3,4-tetrahydronaphthalen-7-yloxy]-N,N-dimethylacetamide (273 mg) and 10% palladium on activated carbon (60 mg) were suspended in ethanol (5.5 ml). After the mixture was stirred at room temperature for 12 hours under hydrogen atmosphere, the catalyst was filtered off and the filtrate was concentrated in vacuo. Recrystallization of the resulting residue from methanol gave 2-[(2S)-2-[[(2R)-2-hydroxy-2-(4-hydroxyphenyl) ethyl]amino]-1,2,3,4-tetrahydronaphthalen-7-yloxy]-N,N-dimethylacetamide (200 mg) having a melting point of 169–172° C.

IR (KBr): 3255, 1656 cm$^{-1}$ $^1$H-NMR (DMSO-d$_6$) δ ppm:1.70–1.85 (1H, m), 2.20–2.30 (1H, m), 2.60–2.90 (6H, m), 2.98 (3H, s), 3.00–3.25 (3H, m), 3.35–3.50 (1H, m), 4.73 (2H, s), 4.80–4.95 (1H, m), 6.02 (1H, br s), 6.65 (1H, d, J=2.6 Hz), 6.70 (1H, dd, J=8.4, 2.6 Hz), 6.78 (2H, d, J=8.5 Hz), 6.99 (1H, d, J=8.4 Hz), 7.22 (2H, d, J=8.5 Hz), 8.80 (1H, br), 9.47 (1H, br s)

Optical rotation (hydrochloride): $[\alpha]_D^{25}$=−69.3° (c=1.01, H$_2$O)

Example 4

The following compounds were prepared according to a similar reaction and treatment to that described in Example 3 using the corresponding amide compound instead of 2-[(2S)-2-[[(2R)-2-(4-benzyloxyphenyl)-2-hydroxyethyl] amino]-1,2,3,4-tetrahydronaphthalen-7-yloxy]-N,N-dimethylacetamide.

1-[2-[(2S)-2-[[(2R)-2-Hydroxy-2-(4-hydroxyphenyl) ethyl]-amino]-1,2,3,4-tetrahydronaphthalen-7-yloxy]acetyl] piperidine amorphous IR (KBr): 3309, 1638 cm$^{-1}$ $^1$H-NMR (DMSO-d$_6$) δ ppm:1.35–1.65 (6H, m), 1.70–1.90 (1H, m), 2.20–2.35 (1H, m), 2.60–2.90 (3H, m), 3.00–3.50 (8H, m), 4.71 (2H, s), 4.85–5.00 (1H, m), 6.02 (1H, br s), 6.66 (1H, s), 6.71 (1H, dd, J=8.4, 2.2 Hz), 6.78 (2H, d, J=8.4 Hz), 6.99 (1H, d, J=8.4 Hz), 7.22 (2H, d, J=8.4 Hz), 8.90 (1H, br), 9.50 (1H, s)

Optical rotation: $[\alpha]_D^{25}$=−85.2° (c=0.58, MeOH)

4-[2-[(2S)-2-[[(2R)-2-Hydroxy-2-(4-hydroxyphenyl) ethyl]-amino]-1,2,3,4-tetrahydronaphthalen-7-yloxy]acetyl] morpholine melting point: 98–101° C. (recrystallizing solvent: chloroform-diethyl ether)

IR (KBr): 3393, 1643 cm$^{-1}$ $^1$H-NMR (DMSO-d$_6$) δ ppm: 1.65–1.80 (1H, m), 2.10–2.25 (1H, m), 2.60–3.20 (6H, m), 3.25–3.65 (10H, m), 4.70–4.90 (3H, m), 5.88 (1H, br), 6.66 (1H, d, J=2.5 Hz), 6.71 (1H, dd, J=8.5, 2.5 Hz), 6.77 (2H, d, J=8.5 Hz), 6.99 (1H, d, J=8.5 Hz), 7.21 (2H, d. J=8.5 Hz), 9.45 (1H, br s)

Optical rotation: $[\alpha]_D^{25}$=−68.4° (c=0.98, MeOH)

2-[(2S)-2-[[(2S)-2-Hydroxy-2-(4-hydroxyphenyl)ethyl]-amino]-1,2,3,4-tetrahydronaphthalen-7-yloxy]-N,N-dimethylacetamide melting point: 181–183° C. (recrystallizing solvent: ethanol-ethyl acetate)

IR (KBr): 3156, 1652 cm$^{-1}$ $^1$H-NMR (DMSO-d$_6$) δ ppm: 1.35–1.55 (1H, m), 1.85–2.00 (1H, m), 2.30–3.05 (14H, m), 4.45–4.55 (1H, m), 4.69 (2H, s), 5.10 (1H, br s), 6.59 (1H, d, J=2.6 Hz), 6.63 (1H, dd, J=8.4, 2.6 Hz), 6.69 (2H, d, J=8.5 Hz), 6.93 (1H, d, J=8.4 Hz), 7.14 (2H, d, J=8.5 Hz), 9.22 (1H, s)

Optical rotation: $[\alpha]_D^{25}$=−24.1° (c=1.00, AcOH)

1-[2-[(2S)-2-[[(2S)-2-Hydroxy-2-(4-hydroxyphenyl) ethyl]-amino]-1,2,3,4-tetrahydronaphthalen-7-yloxy]acetyl] piperidine amorphous IR (KBr): 3374, 1634 cm$^{-1}$ $^1$H-NMR (DMSO-d$_6$) δ ppm: 1.45–1.70 (7H, m), 1.95–2.00 (1H, m), 2.40–2.55 (1H, m), 2.65–3.00 (8H, m), 3.45–3.60 (4H, m), 4.60–4.70 (3H, m), 6.58 (1H, d, J=2.7 Hz), 6.69 (1H, dd, J=8.4, 2.7 Hz), 6.78 (2H, d, J=8.5 Hz), 6.96 (1H, d, J=8.4 Hz), 7.15 (2H, d, J=8.5 Hz)

Optical rotation: $[\alpha]_D^{25}$=−14.2° (c=1.00, CHCl$_3$)

4-[2-[(2S)-2-[[(2S)-2-Hydroxy-2-(4-hydroxyphenyl) ethyl]-amino]-1,2,3,4-tetrahydronaphthalen-7-yloxy]acetyl] morpholine amorphous IR (KBr): 3402, 1649 cm$^{-1}$ $^1$H-NMR (DMSO-d$_6$) δ ppm: 1.40–1.75 (2H, m), 1.85–2.00 (1H, m), 2.30–2.95 (7H, m), 3.40–3.65 (8H, m), 4.45–4.55 (1H, m), 4.72 (2H, S), 5.10 (1H, d, J=4.1 Hz), 6.61 (1H, d, J=2.6 Hz), 6.65 (1H, dd, J=8.3, 2.6 Hz), 6.69 (2H, d, J=8.5 Hz), 6.94 (1H, d, J=8.3 Hz), 7.13 (2H, d, J=8.5 Hz), 9.22 (1H, S)

Optical rotation: $[\alpha]_D^{25}$=−15.5° (c=0.49, MeOH)

4-[(2S)-2-[[(2RS)-2-Hydroxy-2-(4-hydroxyphenyl) ethyl]-amino]-1,2,3,4-tetrahydronaphthalen-7-yloxy]-N,N-dimethylbutyramide amorphous IR (film): 3220, 1616 cm$^{-1}$ $^1$H-NMR (DMSO-d$_6$) δ ppm: 1.35–1.75 (2H, m), 1.80–2.00 (3H, m), 2.35–3.00 (14H, m), 3.31 (1H, s), 3.85–3.95 (2H, m), 4.45–4.55 (1H, m), 5.10 (1H, br s), 6.55–6.75 (4H, m), 6.93 (1H, d, J=7.4 Hz), 7.13 (2H, d, J=8.4 Hz), 9.22 (1H, s)

Example 5

2-[(2S)-2-[[(2R)-2-Hydroxy-2-(4-hydroxyphenyl)ethyl]-amino]-1,2,3,4-tetrahydronaphthalen-7-yloxy]-N,N-dimethylacetamide hydrochloride 2-[(2S)-2-[[(2R)-2-Hydroxy-2-( 4-hydroxy-phenyl) ethyl]-amino]-1,2,3,4-tetrahydronaphthalen-7-yloxy]-N,N-dimethylacetamide (210 mg) was suspended in ethanol (10.5 ml), and 1N hydrochloric acid (546 μl) was added to the suspension and the mixture was dissolved by heating. After cooling, collection by filtration of the precipitated crystals gave 2-[(2S)-2-[[(2R)-2-Hydroxy-2-(4-hydroxyphenyl) ethyl]amino]-1,2,3,4-tetrahydronaphthalen-7-yloxy]-N,N-dimethylacetamide hydrochloride (100 mg) having a melting point of 165–168° C.

IR (KBr): 2433, 1652 cm$^{-1}$ $^1$H-NMR (DMSO-d$_6$) δ ppm: 1.70–1.90 (1H, m), 2.15–2.30 (1H, m), 2.60–3.60 (13H, mm), 4.74 (2H, s), 4.80–4.95 (1H, m), 6.06 (1H, d, J=2.8 Hz), 6.66 (1H, d, J=2.6 Hz), 6.72 (1H, dd, J=8.4, 2.6 Hz), 6.79 (2H, d, J=8.6 Hz), 7.01 (1H, d, J=8.4 Hz), 7.24 (2H, d, J=8.6 Hz), 8.65–9.00 (2H, m), 9.48 (1H, s)

Optical rotation: $[\alpha]D^{25}$=−69.3° (c=1.01, H$_2$O)

Example 6

According to a similar manner to that described in Example 5, the following compounds were prepared from 2-[(2S)-2-[[(2R)-2-hydroxy-2-(4-hydroxyphenyl)ethyl] amino]-1,2,3,4-tetrahydronaphthalen-7-yloxy]-N,N-dimethylacetamide using L-tartaric acid or 1N aqueous sulfuric acid solution.

2-[(2S)-2-[[(2R)-2-Hydroxy-2-(4-hydroxyphenyl)ethyl]-amino]-1,2,3,4-tetrahydronaphthalen-7-yloxy]-N,N-dimethylacetamide 0.5 L-tartrate melting point: 178–181° C. (recrystallizing solvent: ethanol)

IR (KBr): 3634, 3360, 2440, 1659, 1616 cm$^{-1}$ $^1$H-NMR (DMSO-d$_6$) δ ppm: 1.50–1.70 (1H, m), 1.95–2.15 (1H, m), 2.40–3.20 (14H, m), 3.40 (2H, br), 3.79 (1H, s), 4.60–4.80 (3H, m), 5.60 (1H, br), 6.63 (1H, d, J=2.6 Hz), 6.67 (1H, dd, J=8.3, 2.6 Hz), 6.73 (2H, d, J=8.5 Hz), 6.96 (1H, d, J=8.3 Hz), 7.18 (2H, d, J=8.5 Hz), 9.30 (1H, br)

Optical rotation: $[\alpha]_D^{25}$=−64.70 (c=1.03, H$_2$O)

2-[(2S)-2-[[(2R)-2-Hydroxy-2-(4-hydroxyphenyl)ethyl]-amino]-1,2,3,4-tetrahydronaphthalen-7-yloxy]-N,N-dimethylacetamide hemisulfate melting point: 202–205° C. (decomposition) (recrystallizing solvent: ethanol)

IR (KBr): 2429, 1638 cm$^{-1}$ $^1$H-NMR (DMSO-d$_6$) δ ppm: 1.50–1.70 (1H, m), 1.95–2.15 (1H, m), 2.30–3.30 (15H, m), 4.60–4.80 (3H, m), 5.60 (1H, br), 6.63 (1H, d, J=2.6 Hz), 6.67 (1H, dd, J=8.4, 2.6 Hz), 6.74 (2H, d, J=8.5 Hz), 6.96 (1H, d, J=8.4 Hz), 7.18 (2H, d, J=8.5 Hz), 9.34 (1H, br s)

Optical rotation: $[\alpha]_D^{25}$=−65.2° (c=0.50, DMSO)

Example 7

According to a similar manner to that described in Example 5, the following compounds were prepared from 1-[2-[(2S)-2-[[(2R)-2-hydroxy-2-(4-hydroxyphenyl)ethyl] amino]-1,2,3,4-tetrahydronaphthalen-7-yloxy]acetyl] piperidine using L-tartaric acid or D-tartaric acid.

1-[2-[(2S)-2-[[(2R)-2-Hydroxy-2-(4-hydroxyphenyl) ethyl]-amino]-1,2,3,4-tetrahydronaphthalen-7-yloxy]acetyl] piperidine 0.5 L-tartrate melting point: 208–210° C. (recrystallizing solvent: ethanol)

IR (KBr): 3373, 1645 cm$^{-1}$ $^1$H-NMR (DMSO-d$_6$) δ ppm: 1.30–1.70 (7H, m), 2.00–2.15 (1H, m), 2.50–3.25 (7H, m), 3.30–3.50 (4H, m), 3.85 (1H, s), 4.60–4.75 (3H, m), 6.64 (1H, d, J=2.6 Hz), 6.67 (1H, dd, J=8.4, 2.6 Hz), 6.73 (2H, d, J=8.5 Hz), 6.96 (1H, d, J=8.4 Hz), 7.19 (2H, d, J=8.5 Hz), 9.20 (1H, br)

Optical rotation: $[\alpha]_D^{25}$=−66.9° (c=0.55, MeOH)

1-[2-[(2S) -2-[[(2R)-2-Hydroxy-2-(4-hydroxyphenyl) ethyl]-amino]-1,2,3,4-tetrahydronaphthalen-7-yloxy]acetyl] piperidine 0.5 D-tartrate melting point: 206–208° C. (recrystallizing solvent: ethanol)

IR (KBr): 3395, 1645 cm$^{-1}$ $^1$H-NMR (DMSO-d$_6$) δ ppm: 1.35–1.70 (7H, m), 2.00–2.15 (1H, m), 2.50–3.20 (7H, m), 3.30–3.50 (4H, m), 3.82 (1H, s), 4.60–4.75 (3H, m), 5.70 (1H, br), 6.63 (1H, d, J=2.7 Hz), 6.67 (1H, dd, J=8.4, 2.7 Hz), 6.73 (2H, d, J=8.5 Hz), 6.96 (1H, d, J=8.4 Hz), 7.18 (2H, d, J=8.5 Hz), 9.30 (1H, br)

Optical rotation: $[\alpha]_D^{25}$=−82.8° (c=0.50, MeOH)

Example 8

According to a similar manner to that described in Example 5, the following compounds were prepared from 4-[2-[(2S)-2-[[(2R)-2-hydroxy-2-(4-hydroxyphenyl)ethyl] amino]-1,2,3,4-tetrahydronaphthalen-7-yloxy]acetyl] morpholine using L-tartaric acid, D-tartaric acid or fumaric acid.

4-[2-[(2S)-2-[[(2R)-2-Hydroxy-2-(4-hydroxyphenyl)ethyl]-amino]-1,2,3,4-tetrahydronaphthalen-7-yloxy]acetyl]morpholine 0.5 L-tartrate melting point: 199–201° C. (recrystallizing solvent: ethanol)

IR (KBr): 3430, 1652 cm$^{-1}$ $^1$H-NMR (DMSO-$d_6$) δ ppm: 1.50–1.70 (1H, m), 2.00–2.15 (1H, m), 2.50–3.20 (7H, m), 3.30–3.70 (8H, m), 3.82 (1H, s), 4.66 (1H, d, J=6.2 Hz), 4.74 (2H, s), 5.70 (1H, br), 6.65 (1H, d, J=2.5 Hz), 6.68 (1H, dd, J=8.4, 2.5 Hz), 6.73 (2H, d, J=8.5 Hz), 6.97 (1H, d, J=8.4 Hz), 7.18 (2H, d, J=8.5 Hz), 9.30 (1H, br)

Optical rotation: $[\alpha]_D^{25}$=−62.6° (c=0.54, MeOH)

4-[2-[(2S)-2-[[(2R)-2-Hydroxy-2-(4-hydroxyphenyl)ethyl]-amino]-1,2,3,4-tetrahydronaphthalen-7-yloxy]acetyl]morpholine 0.5 D-tartrate melting point: 202–204° C. (recrystallizing solvent: ethanol)

IR (KBr): 3423, 1655 cm$^{-1}$ $^1$H-NMR (DMSO-$d_6$) δ ppm: 1.50–1.70 (1H, m), 2.00–2.20 (1H, m), 2.55–3.25 (7H, m), 3.35–3.65 (8H, m), 3.85 (1H, s), 4.68 (1H, dd, J=9.3, 3.0 Hz), 4.74 (2H, s), 5.90 (1H, br), 6.65 (1H, d, J=2.6 Hz), 6.68 (1H, dd, J=8.4, 2.6 Hz), 6.73 (2H, d, J=8.5 Hz), 6.97 (1H, d, J=8.4 Hz), 7.18 (2H, d, J=8.5 Hz), 9.20 (1H, br)

Optical rotation: $[\alpha]_D^{25}$=−71.5° (c=0.54, MeOH)

4-[2-[(2S)-2-[[(2R)-2-Hydroxy-2-(4-hydroxyphenyl)ethyl]-amino]-1,2,3,4-tetrahydronaphthalen-7-yloxy]acetyl]morpholine hemifumarate melting point: 193–197° C. (recrystallizing solvent: ethanol)

IR (KBr): 3459, 1643 cm$^{-1}$ $^1$H-NMR (DMSO-$d_6$) δ ppm: 1.50–1.65 (1H, m), 2.00–2.15 (1H, m), 2.55–3.20 (7H, m), 3.35–3.70 (8H, m), 4.67 (1H, dd, J=9.3, 3.2 Hz), 4.74 (2H, s), 6.46 (1H, s), 6.64 (1H, d, J=2.6 Hz), 6.68 (1H, dd, J=8.3, 2.6 Hz), 6.73 (2H, d, J=8.5 Hz), 6.96 (1H, d, J=8.3 Hz), 7.17 (2H, d, J=8.5 Hz), 9.30 (1H, br)

Optical rotation: $[\alpha]_D^{25}$=−67.0° (c=0.54, MeOH)

Test Example 1
Action of Drugs on the Spontaneous Contractions of Isolated Pregnant Rat Myometrium The uteri of pregnant SD rats (pregnancy day 21) were isolated and longitudinal uterine muscle strips (about 15 mm in length and about 5 mm in width) free from the basal plate were prepared. The experiment was conducted according to the Magnus method. The preparations with a tension of 1 g were exposed to Locke-Ringer solution maintained at 37° C. and gassed with a mixture of 95% of oxygen and 5% of carbon dioxide. Spontaneous contractions of myometrium were induced isometrically via a pressure transducer and recorded on a rectigram. The drug efficacy was evaluated as 50% inhibitory drug concentration (i.e., $EC_{50}$ value) by comparing the total degree of uterine contraction during 5 minutes before the addition of the drug with the total degree of uterine contraction during 5 minutes after the addition of the drug.

Test Example 2
Action of Drugs on the Atrial Contraction of Isolated Rat Atrium

The atria of SD male rats (350 to 400 g in body weight) were isolated and the experiment was conducted according to the Magnus method. The preparations with a tension of 1 g were exposed to Krebs-Henseleit solution maintained at 37° C. and gassed with a mixture of 95% of oxygen and 5% of carbon dioxide. The atrial contraction was induced isometrically via a pressure transducer and recorded on a rectigram. After addition of the drug, its efficacy was evaluated as drug concentration which increases 20 beats per minute of heart rate (i.e., $EC_{20}$ value).

Test Example 3
Acute Toxicity

To 4 female ICR mice of 4 weeks age was administered intravenously 2-[(2S)-2-[[(2R)-2-hydroxy-2-(4-hydroxyphenyl)-ethyl]amino]-1,2,3,4-tetrahydronaphthalen-7-yloxy]-N,N-dimethylacetamide dissolved in saline at dose of 50 mg/kg. No death of animals was observed during 24 hours after the administration.

What is claimed is:

1. A phenylethanolaminotetralincarboxamide compound represented by the general formula:

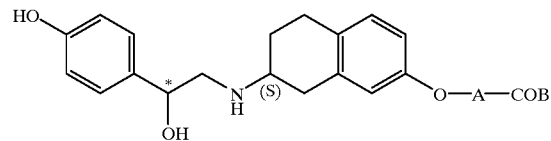

(wherein A represents a lower alkylene group; B represents an amino group, a di(lower alkyl)amino group or a 3 to 7-membered alicyclic amino group which may have an oxygen atom in the ring; the carbon atom marked with * represents a carbon atom in (R) configuration, (S) configuration or a mixture thereof; and the carbon atom marked with (S) represents a carbon atom in (S) configuration) and a pharmaceutically acceptable salt thereof.

2. A phenylethanolaminotetralincarboxamide compound as claimed in claim 1, represented by the general formula:

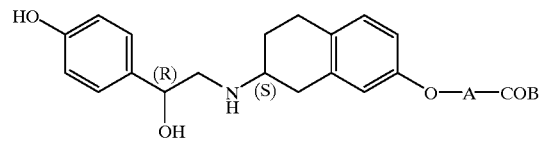

(wherein A represents a lower alkylene group; B represents an amino group, a di(lower alkyl)amino group or a 3 to 7-membered alicyclic amino group which may have an oxygen atom in the ring; the carbon atom marked with (R) represents a carbon atom in (R) configuration; and the carbon atom marked with (S) represents a carbon atom in (S) configuration) and a pharmaceutically acceptable salt thereof.

3. The phenylethanolaminotetralincarboxamide compound as claimed in claim 2, represented by the formula:

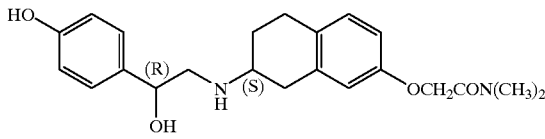

(wherein the carbon atom marked with (R) represents a carbon atom in (R) configuration; and the carbon atom marked with (S) represents a carbon atom in (S) configuration) and a pharmaceutically acceptable salt thereof.

4. A pharmaceutical composition which comprises (a) phenylethanolaminotetralincarboxamide compound represented by the general formula:

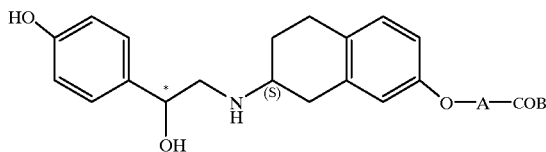

(wherein A represents a lower alkylene group; B represents an amino group, a di(lower alkyl)amino group or a 3 to 7-membered alicyclic amino group which may have an oxygen atom in the ring; the carbon atom marked with * represents a carbon atom in (R) configuration, (S) configuration or a mixture thereof; and the carbon atom marked with (S) represents a carbon atom in (S) configuration) or a pharmaceutically acceptable salt thereof, and (b) a pharmaceutically acceptable carrier or diluent.

5. A pharmaceutical composition as claimed in claim 4 wherein a phenylethanolaminotetralincarboxamide compound is represented by the general formula:

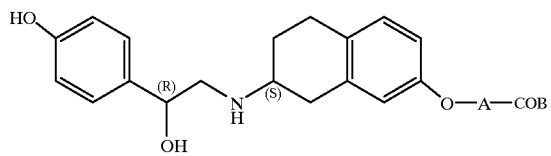

(wherein A represents a lower alkylene group; B represents an amino group, a di(lower alkyl)amino group or a 3 to 7-membered alicyclic amino group which may have an oxygen atom in the ring; the carbon atom marked with (R) represents a carbon atom in (R) configuration; and the carbon atom marked with (S) represents a carbon atom in (S) configuration) or a pharmaceutically acceptable salt thereof.

6. A pharmaceutical composition as claimed in claim 5 wherein the phenylethanolaminotetralincarboxamide compound is represented by the formula:

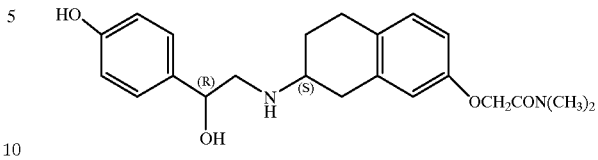

(wherein the carbon atom marked with (R) represents a carbon atom in (R) configuration; and the carbon atom marked with (S) represents a carbon atom in (S) configuration) or a pharmaceutically acceptable salt thereof.

7. A method for the prevention of threatened abortion and premature labor, the prevention and treatment of diseases associated with bronchiostenosis and airway obstruction, or pain remission and promoting stone removal in urolithiasis which comprises administering to a subject in need of the same a therapeutically effective amount of a phenylethanolaminotetralincarboxamide compound represented by the general formula:

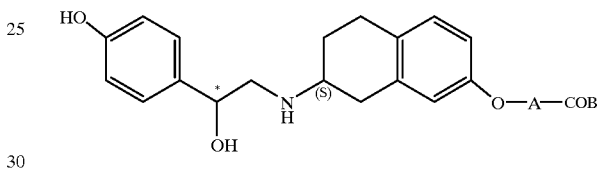

(wherein A represents a lower alkylene group; B represents an amino group, a di(lower alkyl) amino group or a 3 to 7-membered alicyclic amino group which may have an oxygen atom in the ring; the carbon atom marked with * represents a carbon atom in (R) configuration, (S) configuration or a mixture thereof; and the carbon atom marked with (S) represents a carbon atom in (S) configuration) or a pharmaceutically acceptable salt thereof.

* * * * *